United States Patent [19]

Fifolt et al.

[11] 4,374,266
[45] Feb. 15, 1983

[54] AMMONIUM SALTS OF FLUOROPHTHALAMIC ACIDS AND METHOD OF PREPARATION

[75] Inventors: Michael J. Fifolt, Grand Island, N.Y.; Arthur M. Foster, Birmingham, Mich.

[73] Assignee: Occidental Chemical Corporation, Niagara Falls, N.Y.

[21] Appl. No.: 220,672

[22] Filed: Dec. 29, 1980

[51] Int. Cl.³ .......................................... C07C 101/42
[52] U.S. Cl. ..................................... 562/456; 544/94
[58] Field of Search ................... 562/442, 456; 544/94

[56] References Cited

U.S. PATENT DOCUMENTS 1,991,790  2/1935  Cook et al. ........................... 562/442
2,275,006  3/1942  Bindler ................................. 562/442
3,014,033  12/1961  Havart et al. ....................... 562/442

FOREIGN PATENT DOCUMENTS 2328757  1/1975  Fed. Rep. of Germany ...... 562/442
1436810  5/1976  United Kingdom ................ 562/442

OTHER PUBLICATIONS

Shiley et al., J. Fluorine Chem., vol. 2, pp. 19-26, (1972/73).
Finger et al., J. Fluorine Chem., vol. 1, pp. 415-425, (1971/72).
Azuma, Chem. Abst., vol. 77, #141417t, (1972).
Panneitz, Chem. Abst., vol. 92, #60321q, (1980).

*Primary Examiner*—James H. Reamer
*Attorney, Agent, or Firm*—J. F. Tao; A. S. Cookfair

[57] ABSTRACT

Ammonium salts of fluorophthalamic acids characterized by the formula

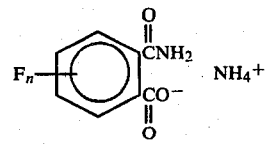

wherein n is 1 or 2, are prepared by the steps of
(A) reacting a chlorophthalic anhydride of the formula

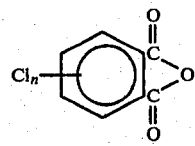

where n is as defined previously, with potassium fluoride or cesium fluoride to form a fluorophthalic anhydride of the formula

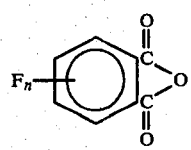

where n is as previously defined, and
(B) reacting the fluorophthalic anhydride with ammonium to form an ammonium salt of a fluorophthalamic acid.

6 Claims, No Drawings

AMMONIUM SALTS OF FLUOROPHTHALAMIC ACIDS AND METHOD OF PREPARATION

BACKGROUND OF THE INVENTION

This invention relates to fluorophthalamic acids and ammonium salts thereof and to a method for the preparation of these compounds. The ammonium fluorophthalamates are particularly useful as chemical intermediates for the preparation of a wide variety of end products including pharmaceuticals and agricultural chemicals such as pesticides, and, in particular, as reactants in novel and advantageous methods for the synthesis of fluoroanthranilic acids, fluoroanilines, fluorobenzoic acids and other fluorinated aromatic compounds.

SUMMARY OF THE INVENTION

In accordance with this invention, ammonium fluorophthalamates of the formula

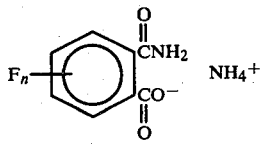

wherein n is 1 or 2, are prepared by a process which comprises (A) reacting a chlorophthalic anhydride of the formula

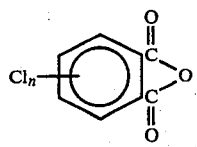

wherein n is as hereinabove defined, with potassium fluoride or cesium fluoride to form a fluorophthalic anhydride of the formula

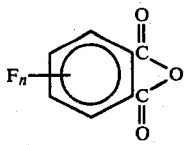

wherein n is as hereinabove defined, (B) reacting the fluorophthalic anhydride with ammonia to form ammonium fluorophthalamate.

The fluorination step of the process that is the preparation of fluorophthalic anhydride by reaction of chlorophthalic anhydride with potassium fluoride or cesium fluoride, may be carried out under a wide range of conditions. The temperature of the reaction may vary considerably for example, from about 75° or lower to 300° Celsius or higher, depending, in part on the particular chlorophthalic anhydride reactant used and whether or not a catalyst is employed. The reaction is preferably carried out in the presence of a catalyst, at a temperature in the range of about 80° to about 280° Celsius. When potassium fluoride is employed as the fluorinating agent, it is preferred to carry out the reaction at higher temperatures, such as about 180° to about 275° Celsius. When cesium fluoride is employed as the fluorinating agent, lower temperatures, such as about 80° to about 200° Celsius are preferred.

The preferred catalysts that may be employed in the fluorination step are polyether catalysts, such as crown ethers, polyethylene glycols, or alkoxy polyethylene glycols, such polyethers typically having a molecular weight ranging from about 200 to about 25,000. Typically, the catalysts are employed in amounts of about 0.1 to about 20 percent, and preferably about 5.0 to about 15 percent by weight, based on the amount of chlorophthalic anhydride.

The fluorination reaction is preferably and conveniently carried out under atmospheric pressure conditions. However, super-atmospheric and sub-atmospheric conditions may be employed, if desired.

It is preferred, but not essential, to employ a catalyst when potassium fluoride is used as the fluorinating agent. When cesium fluoride is used, a catalyst may be employed, but is not preferred, due to the higher reactivity of that fluorinating agent.

Although it is preferred to run the fluorination reaction neat, an inert solvent, such as dipolar aprotic solvent may be employed if desired. Suitable solvents include, for example, dimethylsulfoxide; dimethylformamide; N-methyl-2-pyrrolidinone; sulfolane; hexamethylphosphoramide, and the like.

The proportion of reactants for the fluorination step may vary widely. Generally it is preferred to employ about 20 to about 25 percent molar excess of potassium fluoride or cesium fluoride fluorinating agent.

The ammonolysis of the fluorophthalic anhydride may be carried out over a wide range of temperatures. The preferred reaction temperature is about −50° to about 100°, and most preferably about −10° to about 40° Celsius. Lower temperatures may be employed but are generally unnecessary and uneconomical. At temperatures above about 40° Celsius, depending on the particular fluorophthalamic acid being prepared, the concurrent formation of the fluorophthalimide may occur.

To achieve high yields of the ammonium fluorophthalamate it is preferred to employ the ammonia reactant in excess of about two molar equivalents of $NH_3$ per mole of fluorophthalic anhydride. The preferred ammonia reactant is anhydrous ammonia. Aqueous ammonia may be employed, if desired, but is not preferred since it has been found to encourage the formation of by-products, such as fluorophthalic acids.

The process is preferably carried out at about atmospheric pressure, although super-atmospheric pressures may be employed, if desired. Generally, subatmospheric pressures are avoided, due to the volatility of the ammonia reactant.

It is preferred to carry out the ammonolysis reaction in a suitable solvent, particularly a solvent that will dissolve the fluorophthalic anhydride and that is substantially unreactive with ammonia. Suitable solvents include, for example, acetonitrile, methylene chloride, low molecular weight methoxy ethyleneglycols, such as dimethoxyethane, dimethoxy diethyleneglycol and the like.

The ammonium fluorophthalamate may be converted to the corresponding fluorophthalamic acid by acidification. Typically, the fluorophthalamate is dissolved in a minimum amount of water and the solution is acidified to a pH of about 1.5 to about 6.0 by addition of an acid such as HCl, $H_2SO_4$, $H_3PO_4$, HBr, HI, HF, $HNO_3$ or the like. The fluorophthalmic acid may then be recovered by precipitation or by removal of the water, e.g. by low temperature evaporation or distillation.

The ammonium fluorophthalamates of this invention are particularly useful as novel reactants in a novel and advantageous method for the preparation of fluoroanthranilic acids and fluoroanilines.

Fluoroanthranilic acids and fluoroanilines may be prepared by (A) reacting an ammonium fluorophthalamate of the formula

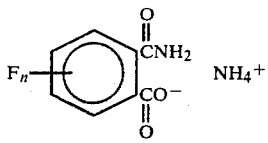

where n is 1 or 2, with an alkali metal or alkaline earth metal hypochlorite to form the corresponding fluoroanthranilic acid; and (B) decarboxylating the fluoroanthranilic acid by reaction with a mineral acid to form the corresponding fluoroaniline of the formula

where n is as previously defined.

The fluoroanthranilic acid produced in step (a) above may be recovered separately. The fluoroanthranilic acids are useful intermediates in the preparation of various other fluorinated aromatic compounds. For example, the fluoroanthranilic acid may be reacted in an acidid medium such as hydrochloric acid with sodium nitrite to prepare fluorobenzoic acids.

The preparation of fluoroanthranilic acids (step A) by reaction of an ammonium fluorophthalamate with an alkaline or alkaline earth metal hypochlorite, preferably sodium hypochlorite may be carried out over a wide range of temperatures, typically between about 40° and about 100°, and most preferably between about 60° and about 80° Celsius. It has further been found advantageous to add the alkaline or alkaline earth metal hypochlorite in combination with a strong base such as an alkali metal or alkaline earth metal hydroxide, preferably sodium hydroxide. It has been found that this preferred reaction scheme, is of benefit in minimizing the formation of undesired by-products. In a preferred method the fluoroanthranilic acids are prepared by reacting an ammonium fluorophthalamate with about 0.5 to 5.0 moles, preferably about 1.0 to about 1.5 moles of alkali or alkaline earth metal hydroxide and about 1.0 to about 5.0 moles, preferably about 1.0 to about 1.5 moles of an alkali or alkaline earth metal oxychloride.

The decarboxylation of the fluoroanthranilic acid is carried out by reaction with an aqueous mineral acid, such as hydrochloric acid, hydrofluoric acid, hydrobromic acid, sulfuric acid, nitric acid, phosphoric acid, and the like. The preferred acid is sulfuric acid. The reaction may be carried out over a wide range of temperatures, such as from about 20° to the reflux temperature of the reaction mixture. Preferably the temperature is maintained in a range of about 75° to about 100° Celsius. The reaction is preferably carried out at atmospheric pressure. Subatmospheric or superatmospheric pressures may be employed but are not generally preferred.

The following specific examples are provided to further illustrate this invention and the manner in which it may be carried out. It will be understood, however, that the specific details given in the examples have been chosen for purpose of illustration and are not to be construed as a limitation on the invention. In the examples, unless otherwise indicated, all parts and percentages are by weight and all temperatures are in degrees Celsius.

EXAMPLE 1

(A) A mixture of 58.0 parts of anhydrous potassium fluoride, 21.7 parts of 4,5-dichlorophthalic anhydride, and 2.0 parts of Carbowax ® m-peg 2000 catalyst was charged to a reactor, heated to about 175° C., and maintained thereat for about 54 hours. The product was removed from the reaction mixture by vacuum distillation and purified by recrystallization from a chloroform-hexane mixture to yield 12.15 parts of 4,5-difluorophthalic anhydride (66% yield) having a melting point of about 94°–96° C.

(B) Acetonitrile (117.5 parts) was charged to a reaction vessel and anhydrous ammonia was bubbled in until the acetonitrile was saturated. The flow of ammonia was continued while a solution of 5.52 parts of the 4,5-difluorophthalic anhydride in 23.5 parts of acetonitrile was added slowly over a 15 minute period. A white precipitate formed. The reaction mixture was stirred for an additional 30 minutes. The acetonitrile was then removed by vacuum distillation to yield 6.1 parts of ammonium salt of 4,5-difluorophthalamic acid.

(C) A portion of the ammonium salt was dissolved in a minimum amount of water, acidified by addition of concentrated hydrochloric acid to a pH of about 2.0, and re-crystallized from water. Analysis of the final product by $C^{13}$ nuclear magnetic resonance and infrared spectroscopy confirmed it to be 4,5-difluorophthalamic acid.

(D) One part of the 4,5-difluorophthalamic acid was heated to 170° C. for a period of 30 minutes, then cooled, dissolved in toluene and crystallized therefrom. The crystalline product was separated by filtration to yield 0.56 parts of 4,5-difluorophthalimide, having a melting range of 154°–156° C. The structure was confirmed by $C^{13}$ nuclear magnetic resonance analysis.

EXAMPLE 2

(A) A mixture of 58.0 parts of anhydrous potassium fluoride, 21.7 parts of 4,5-dichlorophthalic anhydride and 0.5 parts of 18-crown-6, crown ether catalyst, was charged to a reactor and heated at about 150° C. for about 6.5 hours. The product was separated from the reaction mixture and recrystallized as in Example 1A to yield 11.6 parts of 4,5-difluorophthalic anhydride (63% yield) having a melting range of about 94°–96° C.

(B) Following the procedure of Example 1B, the 4,5-difluorophthalic anhydride product was reacted with ammonia to form the ammonium 4,5-difluorophthalamate.

EXAMPLE 3

(A) A mixture of 20 parts of 3-chlorophthalic anhydride, and 20 parts of anhydrous potassium fluoride was heated and maintained at about 235° C. for about 9 hours. The reaction mixture was then cooled and the crude product was removed by vacuum distillation and recrystallized from chloroform to yield 12.65 parts of purified 3-fluorophthalic anhydride (69% yield).

(B) Ten parts of the 3-fluorophthalic anhydride was dissolved in 78.3 parts of acetonitrile and ammonia was bubbled into the solution until no 3-fluorophthalic anhydride could be detected (by thin layer chromatography on silica gel with a 7:2:1 mixture of toluene:ethyl acetate:acetic acid). The acetonitrile was then removed under reduced pressure to yield 14.8 parts of white solid - a mixture of the ammonium salts of 3- and 6-fluorophthalamic acid.

EXAMPLE 4

A first solution of 3.32 parts of 3-fluorophthalic anhydride in 43 parts of dimethoxyethane was prepared. Separately, 86 parts of dimethoxyethane was added to a reaction vessel and ammonia was bubbled in to form a saturated solution of ammonia in dimethoxyethane. The ammonia addition was continued to maintain an excess while the 3-fluorophthalic anhydride solution was added to the ammonia/dimethoxyethane solution, slower with stirring over a 40 minute period. During the addition of reactants, the reaction mixture was maintained under an atmosphere of nitrogen. When all of the 3-fluorophthalic anhydride had been added, the ammonia addition was stopped and the reaction mixture was stirred for an additional five minute period to assure completion of the reaction. The dimethoxyethane was removed under reduced pressure. The remaining crude product was analyzed by $C^{13}$ nuclear magnetic resonance method and found to contain about 75% of the ammonium salt of 3-fluorophthalamic acid.

EXAMPLE 5

A mixture of 20 parts of anhydrous potassium fluoride, 20 parts of 4-chlorophthalic anhydride and 2 parts of Carbowax ® m-peg 2000 catalyst was charged to a reaction vessel and heated at 220° C. for about 18 hours. The product was removed by distillation, then recrystallized from a chloroform-hexane solution to yield 8.13 parts of 4-fluorophthalic anhydride having a melting point of 76°–78° C. Following the procedure of Example 3B, the fluorophthalic anhydride is reacted with ammonia to yield the ammonium salts of a mixed 4- and 5-fluorophthalamic acid.

EXAMPLE 6

(A) Dimethoxyethane (43 parts) was charged to a reactor and ammonia was bubbled in to form a saturated solution. The ammonia addition was continued while a solution of 1.84 parts of 4,5-difluorophthalic anhydride in 13 parts of dimethoxyethane was added slowly over a period of 0.5 hours. The reaction mixture was stirred for an additional 5 minute period and the dimethoxyethane was removed by vacuum distillation. The remaining white solid (the ammonium salt of 4,5-difluorophthalamic acid) was dissolved in 20 parts of aqueous sodium hydroxide (40% NaOH) and the solution was de-gassed under moderately reduced pressure to remove any remaining ammonia; then heated at atmospheric pressure, to 50° C. and maintained at that temperature while 14.1 parts of a 5.78% aqueous sodium hypochlorite solution was added. The solution was then heated to 60°–65° C. and maintained at that temperature, with stirring for about 30 minutes; then cooled to about 20°–25° C. and acidified to a pH of 4–6, by addition of concentrated hydrochloric acid. A precipitate formed and the mixture was extracted with chloroform. The acidification procedure was repeated until no additional precipitate formed. The combined extracts were dried over anhydrous sodium sulfate, filtered, and the chloroform removed by vacuum distillation to yield 1.34 parts of solid 4,5-difluoroanthranilic acid having a melting point of 180°–181° C. The chemical structure of the product was confirmed by infra-red analysis.

(B) A solution of 0.8 parts of 4,5-difluoroanthranilic acid in 40 parts of 1 N sulfuric acid was placed in a reaction vessel equipped with a reflux condenser. The reaction solution was refluxed for 70 hours, then cooled, basified to a pH of about 8.0–9.0 by addition of 1 N sodium hydroxide, saturated with sodium chloride and extracted with diethyl ether. The mixture was then dried over anhydrous sodium sulfate, filtered, and the diethyl ether removed under reduced pressure to yield 0.54 parts of product. Chromatographic analysis of the product indicated a 78% yield (based on the 4,5-difluoroanthranilic acid) of 96% pure 3,4-difluoroaniline. The structure of the 3,4-difluoroaniline product was confirmed by $C^{13}$ NMR.

What is claimed is:

1. Ammonium salts of fluorophthalamic acids, characterized by the formula

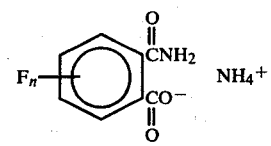

wherein n is 1 or 2.

2. Ammonium-4,5-difluorophthalamate.
3. Ammonium-4-fluorophthalamate.
4. Ammonium-5-fluorophthalamate.
5. Ammonium-3-fluorophthalamate.
6. Ammonium-6-fluorophthalamate.

* * * * *